US00RE47683E

(19) United States
(12) Reissued Patent
Geist et al.

(10) Patent Number: US RE47,683 E
(45) Date of Reissued Patent: *Nov. 5, 2019

(54) K-WIRE AND METHOD FOR SURGICAL PROCEDURES

(71) Applicant: Orthovita, Inc., Malvern, PA (US)

(72) Inventors: Wyatt Drake Geist, Davie, FL (US); Arden Allen Geist, Sr., Indialantic, FL (US)

(73) Assignee: Orthovita, Inc., Malvern, PA (US)

( * ) Notice: This patent is subject to a terminal disclaimer.

(21) Appl. No.: 15/938,565

(22) Filed: Mar. 28, 2018

Related U.S. Patent Documents

Reissue of:
(64) Patent No.: 8,979,889
Issued: Mar. 17, 2015
Appl. No.: 14/269,984
Filed: May 5, 2014

U.S. Applications:
(63) Continuation of application No. 15/454,674, filed on Mar. 9, 2017, now Pat. No. Re. 46,855, which is an application for the reissue of Pat. No. 8,979,889, which is a continuation of application No. 13/974,747, filed on Aug. 23, 2013, now Pat. No. 8,715,311, which is a continuation-in-part of application No. 13/722,641, filed on Dec. 20, 2012,
(Continued)

(51) Int. Cl.
*A61M 29/00* (2006.01)
*A61B 17/88* (2006.01)
*A61B 17/56* (2006.01)

(52) U.S. Cl.
CPC .... *A61B 17/8897* (2013.01); *A61B 2017/564* (2013.01)

(58) Field of Classification Search
CPC ..... A61F 2/958; A61M 20/02; A61M 2/95
USPC ..... 606/198, 313, 326–327; 604/164.13
See application file for complete search history.

(56) References Cited

U.S. PATENT DOCUMENTS 4,654,028 A 3/1987 Suma
4,909,789 A 3/1990 Taguchi et al.
(Continued)

FOREIGN PATENT DOCUMENTS

JP 10057398 3/1998
JP H1057398 A 3/1998
(Continued)

OTHER PUBLICATIONS

Extended European Search Report for Application No. 15198750.0 dated Apr. 8, 2016.
(Continued)

*Primary Examiner* — Beverly M Flanagan
(74) *Attorney, Agent, or Firm* — Lerner, David, Littenberg, Krumholz & Mentlik, LLP

(57) ABSTRACT

A surgical guide wire or K-wire and method of use are provided. The K-wire or guide wire has opposite end portions and a shank portion in between. One end portion has a deformable end portion that, once outside of a confining guide passage, can be deformed to present a projected forward facing area that is larger than the transverse cross section of the K-wire or guide wire while in the passage. The increased area will provide increased resistance to additional forward axial movement into the surgical site.

20 Claims, 4 Drawing Sheets

Related U.S. Application Data now Pat. No. 8,540,747, which is a continuation-in-part of application No. 12/823,791, filed on Jun. 25, 2010, now Pat. No. 8,361,102.

(60) Provisional application No. 61/220,828, filed on Jun. 26, 2009.

(56) References Cited

U.S. PATENT DOCUMENTS

| | | | |
|---|---|---|---|
| 5,026,379 | A | 6/1991 | Yoon |
| 5,217,484 | A | 6/1993 | Marks |
| 5,353,784 | A | 10/1994 | Nady-Mohamed |
| 5,431,651 | A | 7/1995 | Goble |
| 5,431,657 | A | 7/1995 | Rohr |
| 5,433,723 | A | 7/1995 | Lindenberg et al. |
| 5,509,919 | A | 4/1996 | Young |
| 5,512,037 | A | 4/1996 | Russell et al. |
| 5,607,446 | A | 3/1997 | Beehler et al. |
| 5,653,716 | A | 8/1997 | Malo et al. |
| 5,749,887 | A | 5/1998 | Heske et al. |
| 5,795,308 | A | 8/1998 | Russin |
| 6,478,776 | B1 | 11/2002 | Rosenman et al. |
| 6,482,178 | B1 | 11/2002 | Andrews et al. |
| 6,730,061 | B1 | 5/2004 | Cuschieri et al. |
| 7,087,040 | B2 | 8/2006 | McGuckin, Jr. et al. |
| 7,169,160 | B1 | 1/2007 | Middleman et al. |
| 7,367,975 | B2 | 5/2008 | Malecki et al. |
| 7,517,348 | B2 | 4/2009 | Vetter et al. |
| 7,575,578 | B2 | 8/2009 | Wetzler et al. |
| 7,637,945 | B2 | 12/2009 | Solem et al. |
| 7,766,812 | B2 | 8/2010 | Schroeder et al. |
| 7,914,493 | B2 | 3/2011 | Venbrux et al. |
| 8,048,030 | B2 | 11/2011 | McGuckin, Jr. et al. |
| 8,142,416 | B2 | 3/2012 | Stauber |
| 8,361,102 | B2 | 1/2013 | Geist et al. |
| 8,364,280 | B2 | 1/2013 | Marnfeldt et al. |
| 8,398,672 | B2 | 3/2013 | Kleshinski et al. |
| 8,540,676 | B2 | 9/2013 | Geist et al. |
| 8,540,747 | B2 | 9/2013 | Geist et al. |
| 8,545,531 | B2 | 10/2013 | Geist et al. |
| 8,702,720 | B2 | 4/2014 | McLaren |
| 8,715,311 | B2 | 5/2014 | Geist et al. |
| 8,728,111 | B2 | 5/2014 | Geist et al. |
| 2002/0188275 | A1 | 12/2002 | McGuckin |
| 2005/0033236 | A1 | 2/2005 | Wijay et al. |
| 2005/0267555 | A1 | 12/2005 | Marnfeldt et al. |
| 2006/0064101 | A1 | 3/2006 | Arramon |
| 2007/0191778 | A1* | 8/2007 | Venbrux et al. ..... 604/164.13 |
| 2007/0239159 | A1 | 10/2007 | Altarac et al. |
| 2007/0270896 | A1 | 11/2007 | Perez-Cruet |
| 2008/0071223 | A1 | 3/2008 | Stauber |
| 2009/0182245 | A1 | 7/2009 | Zambelli |
| 2009/0275946 | A1 | 11/2009 | Duncan |
| 2010/0057141 | A1 | 3/2010 | Abdelgany et al. |
| 2010/0268029 | A1 | 10/2010 | Phan et al. |
| 2010/0331893 | A1 | 12/2010 | Geist et al. |
| 2011/0230700 | A1 | 9/2011 | Sing et al. |
| 2013/0110118 | A1 | 5/2013 | Geist et al. |

FOREIGN PATENT DOCUMENTS

| | | | |
|---|---|---|---|
| JP | 2008528109 | A | 7/2008 |
| WO | 2006078743 | A1 | 7/2006 |
| WO | 2007106081 | A2 | 9/2007 |

OTHER PUBLICATIONS

PCT/US2010/040032 International Search Report dated Feb. 4, 2011.

PCT/US2010/040032 Written Opinion of the International Searching Authority dated Dec. 26, 2011.

* cited by examiner

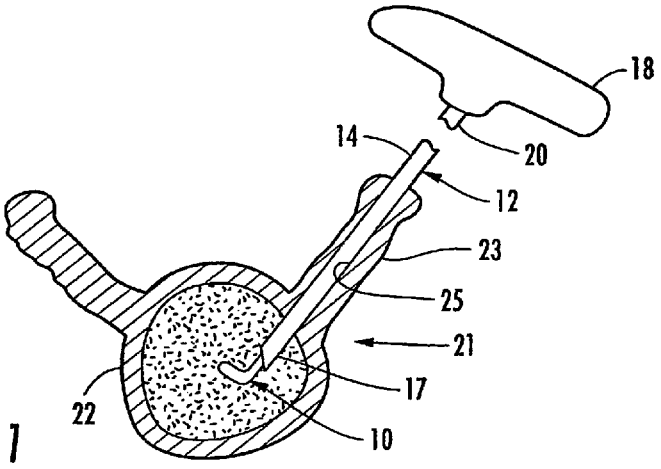
FIG. 1
FIG. 2A
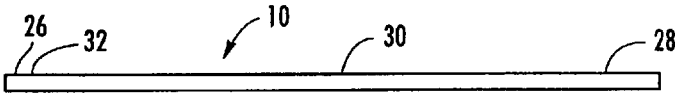
FIG. 2B
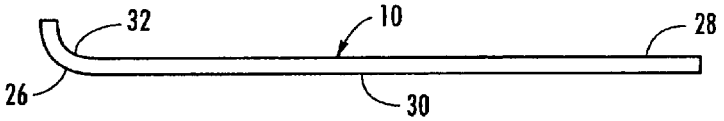
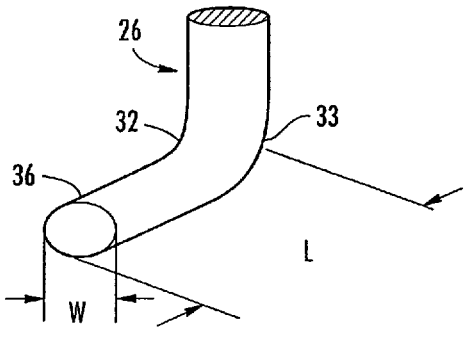
FIG. 3

K-WIRE AND METHOD FOR SURGICAL PROCEDURES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATION

In accordance with 37 C.F.R 1.76, a claim of priority is included in an Application Data Sheet filed concurrently herewith. Accordingly, under 35 U.S.C. §119(e), 120, 121, and/or 365(c), the present [invention] *application is a continuation reissue of U.S. application Ser. No. 15/454,674 filed on Mar. 9, 2017, and both the present application and U.S. application Ser. No. 15/454,674 are reissue applications of U.S. application Ser. No. 14/269,984 filed on May 5, 2014, entitled "K-Wire and Method for Surgical Procedures" now issued U.S. Pat. No. 8,979,889, which issued on Mar. 17, 2015, which* claims priority as a continuation of U.S. Non-Provisional Utility application Ser. No. 13/974,747, filed Aug. 23, 2013, entitled, "[K-WIRE AND METHOD FOR SURGICAL PROCEDURES] *K-Wire and Method for Surgical Procedures", now issued U.S. Pat. No. 8,715,311, which issued on May 6, 2014,* which is a continuation-in-part to U.S. Non-Provisional Utility application Ser. No. 13/722,641, filed Dec. 20, 2012, entitled, "[K-WIRE AND METHOD FOR SURGICAL PROCEDURES] *K-Wire and Method for Surgical Procedures*", now issued U.S. Pat. No. 8,540,747, which issued on Sep. 24, 2013, which is a continuation-in-part to U.S. Non-Provisional Utility application Ser. No. 12/823,791, filed Jun. 25, 2010, entitled, "[K-WIRE AND METHOD FOR SURGICAL PROCEDURES] *K-Wire and Method for Surgical Procedures*", now issued U.S. Pat. No. 8,361,102, which issued on Jan. 29, 2013, which claims priority to U.S. Provisional Patent Application No. 61/220,828, filed Jun. 26, 2009, entitled, "[K-WIRE AND METHOD FOR SURGICAL PROCEDURES] *K-Wire and Method for Surgical Procedures*". The contents of each of the above referenced applications are herein incorporated by reference in its entirety.

FIELD OF INVENTION

The present invention relates to an improved guide wire or K-wire for use in surgical procedures such as orthopedic procedures, and in particular, spinal procedures such as percutaneous pedicle screw constructs.

BACKGROUND OF THE INVENTION

In certain surgical procedures, a K-wire (Kirschner wire) or guide wire is used in combination with a surgical tool such as a jamshidi needle. The jamshidi needle is used to form a hole through bone as a first step in certain medical procedures like attaching a screw to a pedicle. The K-wire or guide wire is inserted through the needle into the interior of the bone, which, if not done properly, can injure the patient, particularly if it engages certain sensitive parts which may include breaching the anterior cortex of a vertebral body. The K-wire or guide wire is used as a portal for certain surgical steps like guiding a tap, screw or screwdriver to the surgical site. The procedures oftentimes require the use of force which can cause a properly positioned K-wire or guide wire to move forward into the surgical site, which, if excessive, can move into contact where contact is to be avoided.

A K-wire or guide wire is generally cylindrical and has a diameter of about 3 millimeters, making it easy to move during use. In fact, the K-wire or guide wire is designed to move during its installation; however, once installed its movement is not impeded, requiring care in its use. The cross sectional size of the K-wire though is limited by the tools and devices it is used with. Each tool or device is provided with a through bore for receiving the K-wire or guide wire, limiting the size and type of wire that can be used. Additionally, the K-wire is typically removed by passing through a through bore in a device or tool. Thus, to date, only K-wires with a small diameter, generally cylindrical round cross section, have been used which presents the problem in their use. It should also be noted that while the K-wires or guide wires illustrated herein include a solid center core, the K-wire or guide wire may be a hollow tubular member without departing from the scope of the invention.

The present invention provides a solution to this problem by providing an improved K-wire or guide wire which, when inserted, provides increased resistance to forward axial movement while still being usable with traditional surgical tools and devices.

DESCRIPTION OF THE PRIOR ART

U.S. Pat. No. 5,431,651 discloses a cross pin and set screw femoral and tibial fixation device for mounting a ligament graft. The device includes a drill guide for drilling a transverse hole. The drill guide is releasable from a first twist drill so as to leave it in place. The first twist drill is used to guide further drilling and passage of a fastener device. A K-wire or the first twist drill is used for guiding a second twist drill for enlarging the transverse hole and for guiding and turning a cannulated fastener device into a femoral bone end of the ligament graft. There is no feature on the K-wire to limit the extent of its insertion subsequent to it passing through the bone.

U.S. Pat. No. 7,575,578 discloses a surgical drill guide including a handle and an arm having an end which contacts a bone. The handle includes a plurality of slots or channels which receive a sleeve. The sleeve is used to guide a K-wire into the bone. The K-wire serves as a guide for drilling a tunnel into the bone. The K-wire does not include a feature to limit the extent of its insertion subsequent to it passing through the bone.

U.S. Published Patent Application No. 2007/0239159 discloses devices and a system for placing bone stabilization components in an individual. In particular, the bone stabilization components are placed on the spine. Various tools, including a K-wire, are employed to properly locate, place and secure the devices in an individual.

U.S. Published Patent Application No. 2007/0270896 discloses a device for accessing the pedicle of a vertebra including a Jamshidi needle.

SUMMARY

The present invention involves the provision of a K-wire which can be used with traditional surgical tools and devices. The inventive guide wire or K-wire has an end portion that, upon exit from the through bore of a surgical tool or device, can be changed in a controlled manner to present a deformable end portion that will provide a forward face with a larger projected area than the end surface of the K-wire while in the through bore. The deformation may be induced mechanically from internal stress, thermally or otherwise.

The present invention also involves the provision of a method of conducting surgery utilizing a guide wire or K-wire. The method includes passing a guide wire or K-wire through a tool or device into a surgical slit with the guide wire or K-wire presenting a forward facing area of a first size. The guide wire or K-wire then has an end portion moved out of the tool or device where the forward end portion can be expanded to present a forward facing area of a second size larger than the first size. After use, the guide wire or K-wire may be extracted from the surgical site through a surgical tool or device.

BRIEF DESCRIPTION OF THE DRAWINGS

FIG. 1 is a schematic plan view of vertebra showing a jamshidi needle extending through a pedicle;

FIGS. 2A, 2B are side elevation views of a K-wire or guide wire showing two configurations of one end portion of the K-wire or guide wire;

FIG. 3 is an enlarged fragmentary view of a K-wire or guide wire showing an end portion shown configured to present an expanded forward face;

Like numbers used throughout the Figures designate like or similar parts and/or construction.

DETAILED DESCRIPTION OF THE INVENTION

Figure 4:
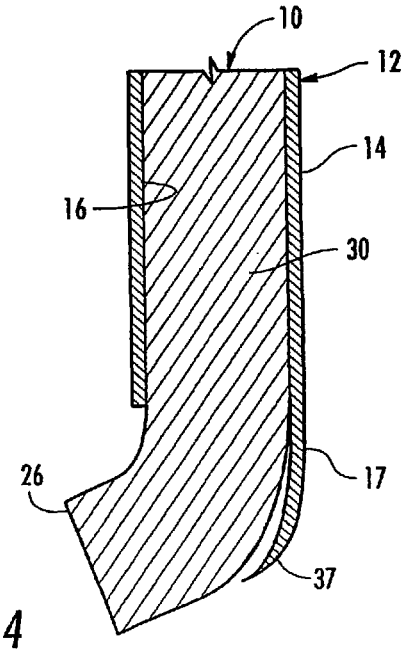
FIG. 4 is a fragmentary side sectional view of a jamshidi needle with a K-wire or guide wire in a through bore.

While the present invention is susceptible of embodiment in various forms, there is shown in the drawings and will hereinafter be described presently preferred embodiments with the understanding that the present disclosure is to be considered an exemplification of the invention and is not intended to limit the invention to the specific embodiments illustrated.

Referring generally to the figures, the reference numeral 10 designates generally a K-wire or guide wire usable in surgical procedures in combination with a surgical tool such as a jamshidi needle 12, drill or tap (not shown), or a surgical device such as a screw, plate or implant. K-wires (also called Kirschner wires) or guide wires are well known in the art. Jamshidi needles are also well known in the art and have a shank 14 with a through bore 16 (as would a drill, tap or screw) and a sharpened distal end 17. A handle 18 may also be provided at the proximal end 20 of the shank 14 for facilitating insertion of the shank into a surgical site 21, such as a vertebra 22 with a pedicle 23 in a patient such as a human. A surgeon may manipulate the jamshidi needle 12 using the handle 18, and may also apply impact force to the shank 14 by striking the handle with a hand or impact tool such as a hammer. Jamshidi needles are used to penetrate bone in the performance of a surgical procedure such as attaching a screw 24 to bone. A rod (not shown) may be installed in the through bore 16 during hole formation to increase rigidity of the shank 14. The rod is removed to provide a through bore 16 for the K-wire 10 insertion. After forming a hole 25 with the jamshidi needle 12, the K-wire or guide wire 10 is inserted into the interior of the bone and the jamshidi needle is removed, leaving the K-wire or guide wire in place. In some surgical procedures, like spinal surgery, the K-wire or guide wire is inserted through one wall of a bone, e.g., a pedicle 23 and is placed against an opposite bone wall. If care is not taken during surgery, the K-wire or guide wire may be pushed through the opposing bone wall creating a risk of injury. The present invention is a solution to this potential problem.

The K-wire or guide wire 10 is typically used as a pilot or guide for other surgical tools or devices such as drills, taps, plates, implants and screws. In the attachment of a screw 24 (FIG. 5B), the screw can have a through bore 44 that receives the K-wire or guide wire for guiding the screw to a drilled and tapped hole 25. After installation of the screw 24, the K-wire or guide wire 10 is then extracted through the through bore 44 of the screw 24 by simply pulling on the K-wire or guide wire to reduce the frontal area of the K-wire or guide wire substantially to its original size.

The K-wire or guide wire 10 has opposite end portions 26, 28 and a generally cylindrical intermediate portion 30 positioned between the end portions. The length of the K-wire or guide wire 10 is preferably long enough to extend beyond both ends of the surgical tool being used, e.g., a jamshidi needle 12. The K-wire or guide wire 10 is sized and shaped to be freely movable along the through bore 16. The end portion 28 will be referred to as the manipulative end and the end portion 26 will be referred to as the operative end for convenience. Preferably, the entire length of the manipulative end portion 28 and the intermediate portion 30 is generally cylindrical to facilitate removal of a tool or device from an installed K-wire or guide wire 10.

The operative end portion 26 is provided with a section 32 that is controllably deformable. The section 32 may be an integral portion of the K-wire or guide wire 10 or attached thereto. Several different sections 32 are described below. In general, the section 32 is configurable to fit within the through bore 16 and freely movable therein. It is insertable into the through bore 16 for insertion into the surgical site 21 for use and for removal from a through bore in the tool or device. The K-wire or guide wire may also be removed prior to a later surgical step if it is no longer needed. For example, if the K-wire or guide wire is not needed to guide the screw 24 for insertion, it may be removed prior to attaching the screw 24. When outside of the through bore 16, the operative end 26 expands automatically or can be manually expanded to present an expanded face with a projected area greater than the transverse cross sectional area of the K-wire or guide wire 10 while positioned in the through bore 16. By way of example, the operative end 26 seen in FIG. 3 has a projected area of approximately (given that the end 33 of the bend at the intermediate section 30 of K-wire or guide wire 10 is rounded reducing the area slightly) L times W whereas the K-wire or guide wire has a cross sectional area of $A=\pi r^2$ where r is equal to W/2. It is preferred that the reconfigured cross sectional projected area be at least about 1.5 times, and preferably at least about twice the size of the first cross sectional area of the K-wire or guide wire as described below.

The K-wire or guide wire 10 or the deformable portion 32 of the K-wire or guide wire may be made of a deformable material which will allow at least the operative end 26 to be configured between first and second configurations (see FIGS. 2A and 2B) with one configuration (FIG. 2B) presenting a larger projected area than the first (FIG. 2A) as discussed above. One suitable reconfigurable material is referred to as a shape memory alloy such as Nitinol. A reversible, solid phase transformation known as martensitic transformation is the force behind shape memory alloys. Such alloys are well known and form a crystal structure which is capable of undergoing a change from one form of crystal structure to another. Temperature change and/or loading can initiate the shape transformation. By way of example, above its transformation temperature, Nitinol is superelastic, able to withstand deformation when a load is applied and return to its original shape when the load is removed. Below its transformation temperature, it displays the shape memory effect. When it is deformed below its transformation temperature, it will remain in that shape until heated above its transformation temperature, at which time it will return to its original shape. The original shape would then be the bent form and then it can be reformed cold to straight. Upon heating, the bend will return. The heat (or temperature increase) can be provided by contact with the patient. Elastically deformable materials may also be used, such as spring steel with high yield strength, where stress is induced to change a shape is elastically released to change the shape of the deformed member back to its non stressed shape. An embodiment of the invention, shown in FIGS. 5A and 5B and described below, could be made using a spring material. Plastically deformable materials might also be used for some operative end portion 26 configurations. The terms resiliently deformable, plastically deformable and spring are used generally to indicate a material property when the material is deformed during typical use of the K-wire or guide wire as described herein. Controlled bending can be induced by using controlled weak points such as a groove or the like at selected strategic locations. The embodiment in FIGS. 5A and 5B might also be used with a plastically deformable material. The screw 24 or other tool or device that is anticipated to be the last one used with the K-wire or guide wire 10 may be provided with a forcing cone 35 to help reconfigure the end portion 26 back to its unexpanded shape to conform it to fit within a passage like passages 16, 44 for insertion or removal. An embodiment of this form is seen in FIGS. 5A and 5B and is described below.

In the embodiment shown in FIGS. 1-3, the operative end 26 has a laterally extending portion 36 when out of the through bore 16. The deformation to lateral extension may be provided as described above by applying heat to effect bending from memory. The portion 36 may be provided as a permanent bend in the K-wire or guide wire 10 which can then be deformed to straight by confinement in the through bore 16, and upon exit from the through bore will reassume its bent configuration. The material properties of the end portion 26 may be selected to provide for straightening of the bend for removal through a passage or bore which may be facilitated, e.g., by the use of a forcing cone 35. The lateral extension presents a larger projected area to further limit forward axial motion into the surgical site.

FIG. 4 shows a surgical tool configuration that can be used to facilitate directing a K-wire or guide wire 10 out of the through bore 16. It uses a curved tip 37 to direct the exiting K-wire or guide wire 10.

Figure 5A:
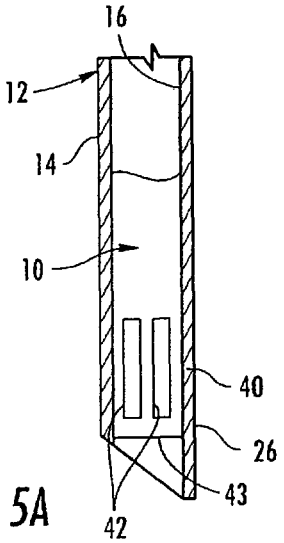
FIGS. 5A and 5B are enlarged fragmentary side views of an end portion of a K-wire or guide wire with one embodiment of reformable end portion.
Figure 5B:
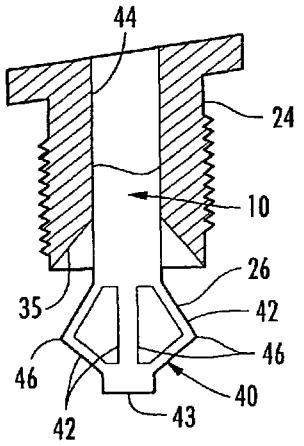

In the embodiment shown in FIGS. 5A and 5B, the operative end 26 is in the form of an expandable cage 40 having a plurality of rods 42 that can assume an extended position; FIG. 5A illustrates a contracted configuration of cage 40 when in a through bore 16 of shank 14. FIG. 5B illustrates the cage 40 in its expanded configuration and a screw positioned on the K-wire or guide wire 10. The embodiment of FIGS. 5A and 5B may be constructed in at least two ways, resiliently deformable rods 42 or plastically deformable rods 42. A memory metal alloy may be used. A polymeric material such as PEEK may also be used for at least the rods 42. If the rods 42 are elastically deformable, they can be formed as biased to an outward or expanded configuration, where once outside of the through bore 16 they will move outwardly to relieve induced stress to provide the expanded configuration like in FIG. 5B. The rods 42 may also be plastically deformable, and upon application of axial force will move to an expanded position as in FIG. 5B. When the K-wire or guide wire is in the through bore 16, the rods 42 assume or are in the collapsed configuration and when the rods 42 are outside of the bore, they assume or are forced into the expanded position providing an increased projected area for engagement with material in the surgical site as discussed above. It is to be noted that the rods may also be made of a memory alloy as described above. The forcing cone 35 may be used to facilitate removal of the K-wire or guide wire 10 through the through bore 44. The distal ends of the rods 42 may be held in place with an end cap 43. The projected area of the end portion 26 when expanded, as seen in FIG. 5B, would be that area defined or bounded by outermost extending portions of the rods 42 as at portions 46.

Figures 6A, 6B, 7, 8, 9:
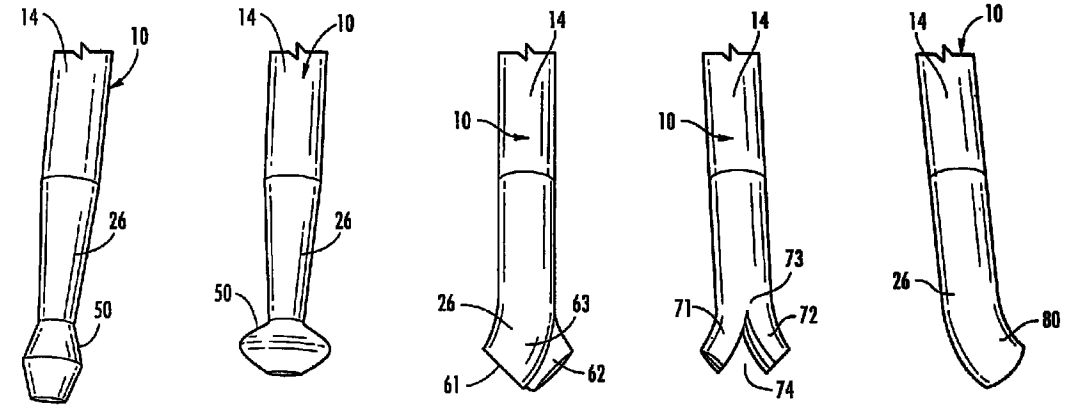
FIGS. 6A and 6B are enlarged side views of an end portion, expanded and unexpanded, of a further embodiment of a K-wire or guide wire of the present invention.
FIG. 7 is an enlarged side view of an end portion of a still further embodiment of a K-wire or guide wire of the present invention.
FIG. 8 is an enlarged side view of an end portion of a still further embodiment of a K-wire or guide wire of an end portion of the present invention.
FIG. 9 is an enlarged side view of an end portion of an embodiment of the invention similar to that shown in FIG. 2B.

FIGS. 6A and 6B illustrate another embodiment of the invention. FIG. 6A shows an end portion 26 with an expandable end bulb 50 that may be made out of a memory alloy that, upon heating, assumes the expanded configuration illustrated in FIG. 6B. This embodiment is particularly adapted for use when extraction of the K-wire or guide wire is other than through a tool or device passage.

FIG. 7 illustrates another embodiment of the invention. It utilizes a pair of opposed legs 61, 62. The legs 61, 62 are constructed to move in an outward direction either from spring action or from otherwise reassuming a formed shape as from a temperature change as by using a memory alloy as described above. In the illustrated embodiment, the legs 61, 62 have overlying portions at 63.

FIG. 8 illustrates an additional embodiment of the invention and is similar to the form shown in FIG. 7 by having two legs 71, 72, but the legs do not overlap; rather the legs diverge from a common area 73 and have a gap 74 therebetween when in the extended position as shown.

The embodiments of the invention shown in FIGS. 6-8 all utilize a shank 14 of one material and an end portion of another material such as a spring material or a memory alloy.

FIG. 9 illustrates a still further embodiment of the present invention. It is similar to the K-wire or guide wire 10 shown in FIG. 2 and has a shank 14 with an attached end portion 26 having a single extending leg 80 shown in its extended configuration. The portion 80 may be provided as a permanent bend in the K-wire or guide wire 10 which can then be deformed to straight by confinement in the through bore 16, and upon exit from the passage will reassume its bent configuration. The material properties of the end portion 80 may be selected to provide for straightening of the bend for removal through a passage which may be facilitated, e.g., by the use of a forcing cone. The lateral extension presents a larger projected area to further limit forward axial motion into the surgical site.

Figure 10:
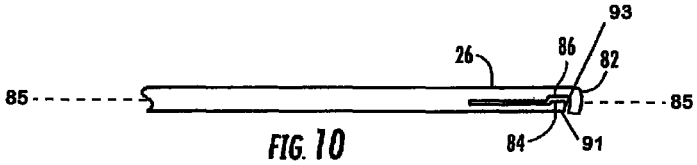
FIG. 10 is an enlarged side view of an end portion of a still further embodiment of the present invention.
Figure 11:
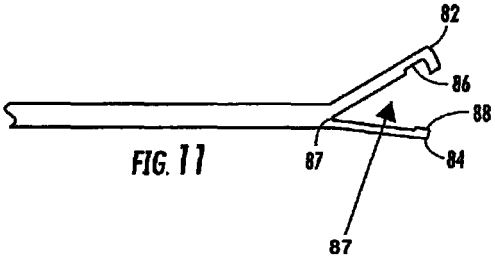
FIG. 11 is an enlarged side view of the embodiment illustrated in FIG. 10 with the end portions spread apart.

FIGS. 10 and 11 illustrate a still further embodiment of the present invention. The end portion 26 of the K-wire or guide wire includes a plurality of deformable ends, illustrated herein as independent legs 82 and 84. The K-wire or guide wire of FIGS. 10 and 11 can be made from a shape memory alloy such as Nitinol. Other shape memory alloys and materials can also be used. The ends 82 and 84 are normally deformed outwardly from the longitudinal axis 85 of the K-wire or guide wire at a common area diverging point 87 as shown in FIG. 11 within the guide wire. As such, the deformable ends, or legs 82 and 84 form separate structures which can move outwardly, independent of each other from the common area diverging point 87. The legs 82 and 84 are separated by a gap 87 which runs the length of the legs 82 and 84 and is orientated in a generally parallel manner from the longitudinal axis 85 of the guide wire 10. The deflection of the ends 82 and 84 presents a larger end surface area when the K-wire or guide wire is penetrating a bone. This larger end surface offers more resistance and consequently prevents the K-wire or guide wire from penetrating too far into the bone and perhaps passing into an adjacent bone or outside of the intended bone. The length of the ends 82 and 84 together with the different shape memory alloys determine how quickly the ends 82 and 84 deform outwardly after they enter a bone. The more rapidly they deform, the less they penetrate into a bone. The ends 82 and 84 collapse together, as shown in FIG. 10, when the K-wire or guide wire is withdrawn back through the Jamshidi needle. A groove 86 on end 82 permits projection 88 to fit therein when in the collapsed position.

As further illustrated, the K-wire or guide wire 10 is shown with one of the deformable ends being longer than the opposing deformable end. As illustrated, leg 82 is longer than leg 84. Leg 82 includes a tip portion 89 that extends past and is bent inwardly towards the leg 84 to overlap a tip portion 91 of the shorter leg 84. While most of the leg 82 is orientated in a generally parallel manner relative to the leg 84, at least a segment of, if not all of the tip portion 89 is positioned in a perpendicular orientation relative to the leg 84. A second gap 93 separates the tip portions 89 and 91. The second gap 93 therefore is formed substantially perpendicular to the longitudinal axis 85 when legs 82 and 84 are in the non-deployed or not separated state.

Figure 12:
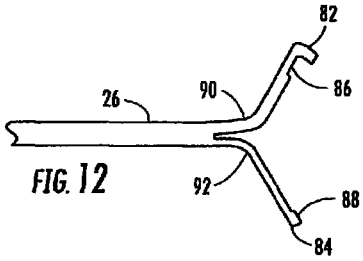
FIG. 12 is an enlarged side view of a still further embodiment of the present invention.
Figure 13:
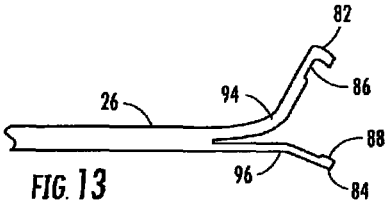
FIG. 13 is an enlarged side view of a still further embodiment of the present invention.

FIGS. 12 and 13 illustrate other embodiments of the present invention. These embodiments are variations of the embodiment illustrated in FIGS. 10 and 11. In FIG. 12 the end 82 of the K-wire or guide wire bends outwardly at 90. Also end 84 bends outwardly at 92. The bends 90 and 92 are positioned within the legs 82 and 84 at some distance away from the common area diverging point 87, i.e. towards the tip portions 89 and 91. This embodiment permits the ends 82 and 84 to bend outwardly from the longitudinal axis more rapidly than the embodiments of FIGS. 10 and 11. In FIG. 13, the end 82 bends outwardly at 94 and the end 84 bends outwardly at 96. Bends 94 and 96 are closer to the tip portions 89 and 91. Thus, they permit the ends 82 and 84 to bend outwardly from the longitudinal axis more rapidly than the bends 90 and 92 of FIG. 12. The faster the ends move away from the longitudinal axis, the less the K-wire or guide wire penetrates into the bone. Therefore, the embodiment of FIG. 13 would penetrate less into a bone than the embodiment of FIG. 12. Also the embodiment of FIG. 12 would penetrate less into a bone than the embodiment of FIGS. 10 and 11.

Figure 14:
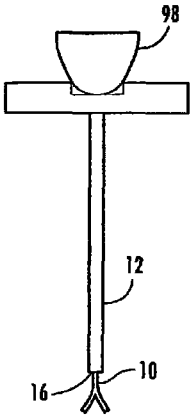
FIG. 14 is a view of the present invention used in a surgical procedure.

The present invention also includes a method of conducting a medical procedure using a K-wire or guide wire, as illustrated in FIG. 14. A surgeon or other medical personnel places a surgical tool end at the surgical site. The initial surgical tool used preferably has a guiding through bore opening at the distal tool end such as that described above for a jamshidi needle 12. A K-wire or guide wire 10 is guided to the site by passing the K-wire or guide wire through the through bore 16 until the operative end 26 extends beyond the open end of the through bore 16. A funnel 98 helps the surgeon place the K-wire or guide wire into the Jamshidi needle. The operative end 26 of the K-wire has at least a portion deformed after its exit from the through bore 16 such that the deformed portion presents a projected area greater than the cross sectional area of the K-wire or guide wire when in the through bore 16 as described above. The deformation can occur automatically as by increasing the temperature of the operative end portion 26 when it includes a memory metal alloy. The deformation may also be induced by relieving stress induced into the operative end portion as when the deformable portion is constructed of a spring material. The deformation may also be induced mechanically by the application of an axially directed force along the K-wire or guide wire 10. After at least a portion of the surgery, the K-wire or guide wire can be removed as described above. The K-wire or guide wire is used to guide surgical tools and/or devices to the surgical site during the surgical procedure. Once the K-wire or guide wire has been inserted into the bone, the jamshidi needle can be withdrawn and a cannulated tap or other instrument can be slid down the K-wire or guide wire and inserted into the bone. When the tap reaches the expanded ends 82, 84 of the K-wire it will stop its forward progress. Thus, this invention avoids the need for fluoroscopy to determine the position of the tap or other instrument in a bone.

It is to be understood that while certain forms of the invention are illustrated, it is not to be limited to the specific forms or arrangements herein described and shown.

It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

[1. A method of conducting a medical procedure using a guide wire, the method including: placing a surgical tool end at a surgical site, said surgical tool having a guiding through bore opening at the tool end; guiding a guide wire to the site by passing the guide wire through the passage, said guide wire having an operative end portion; and deforming a portion of the operative end portion after its exit from the passage such that the deformed portion presents a projected area greater than the cross sectional area of the guide wire when in the passage, wherein said operative end portion comprising a first independent deformable leg and a second independent deformable leg, each said independent deformable leg diverging from a common area of said guide wire, said independent deformable legs predisposed to move in an outward direction with respect to each other and forming a first gap extending the length of said independent deformable legs; one independent deformable leg being longer than said second independent deformable leg, said longer independent deformable leg including a tip portion that is constructed to overlap a tip portion of the said shorter independent deformable leg and forming a second gap between said tip portions, said second gap formed generally perpendicular to the guide wire longitudinal axis when in the non-deformed state, wherein each said opposing deformable legs contains a bend positioned distally from the point where said opposing independent deformable leg diverge from said common area of said guide wire, wherein at least one independent deformable leg contains a groove sized to receive a projection and said opposite independent deformable leg contains a projection sized and shaped to fit within said groove.]

[2. The method of claim 1 wherein the deforming occurs automatically.]

[3. The method of claim 1 wherein the deforming is induced by increasing the temperature of the operative end portion.]

[4. The method of claim 1 wherein the operative end portion has a deformable portion constructed of memory metal alloy.]

[5. The method of claim 1 wherein the deforming is induced by relieving stress induced into the operative end portion when in the guiding passage.]

[6. The method of claim 1 wherein the operative end portion has a deformable portion constructed of a spring material.]

[7. A method of conducting a medical procedure using a K-wire, the method including: placing a surgical tool end at a surgical site, said surgical tool having a guiding through bore opening at the tool end; guiding a K-wire to the site by passing the K-wire through the passage, said K-wire having an operative end portion; and deforming a portion of the operative end portion after its exit from the passage such that the deformed portion presents a projected area greater than the cross sectional area of the K-wire when in the passage, wherein said operative end portion comprising a first independent deformable leg and a second independent deformable leg, each said independent deformable leg diverging from a common area of said K-wire, said independent deformable legs predisposed to move in an outward direction with respect to each other and forming a first gap extending the length of said independent deformable legs; one independent deformable leg being longer than said second independent deformable leg, said longer independent deformable leg including a tip portion that is constructed to overlap a tip portion of the said shorter independent deformable leg and forming a second gap between said tip portions, said second gap formed generally perpendicular to the K-wire longitudinal axis when in the non-deformed state, wherein each said opposing deformable legs contains a bend positioned distally from the point where said opposing independent deformable leg diverge from said common area of said K-wire, wherein at least one independent deformable leg contains a groove sized to receive a projection and said opposite independent deformable leg contains a projection sized and shaped to fit within said groove.]

*8. A method of conducting a medical procedure using a guide wire, the method including:*

*contacting a surgical tool at a surgical site;*

*placing a guide wire through the surgical tool, the guide wire having an operative end portion in a first position while in the surgical tool, the guide wire being monolithic and bifurcating into first and second portions at the operative end portion; and*

*inserting the operative end portion of the guide wire into the surgical site, the operative end portion moving to a second position when inserted in the surgical site,*

*wherein a projected area of the operative end in the second position is greater than a cross sectional area of the operative end in the first position.*

*9. The method of claim 8, wherein the surgical site is a vertebral body.*

*10. The method of claim 8, wherein the first portion includes a first independent deformable leg and the second portion includes a second independent deformable leg, each independent deformable leg diverging from a common area of the guide wire.*

*11. The method of claim 10, wherein the independent deformable legs are predisposed to move in an outward direction with respect to each other to form a first gap extending the length of the independent deformable legs.*

*12. The method of claim 10, wherein each independent deformable leg contains a bend positioned distally from the point where the opposing independent deformable leg diverges from said common area of the guide wire.*

*13. The method of claim 10, wherein at least one independent deformable leg contains a groove sized to receive a projection and the other independent deformable leg contains a projection sized and shaped to fit within the groove.*

*14. The method of claim 8, wherein the first and second portions include substantially linear first and second independent deformable legs, the independent deformable legs being substantially parallel to each other in the first position and diverging from a longitudinal axis of the guide wire in the second position.*

*15. The method of claim 8, wherein the movement between the first and second positions occurs automatically.*

*16. The method of claim 8, wherein the operative end portion has a deformable portion constructed of memory metal alloy.*

*17. The method of claim 8, wherein the movement between the first and second positions is induced by relieving stress induced into the operative end portion when in the surgical tool.*

*18. The method of claim 8, wherein the surgical tool is a jamshidi needle.*

*19. The method of claim 8, further including the step of using the operative end of the guide wire as a marker or a stop for placing a second surgical tool.*

*20. The method of claim 8, further including the step of removing the surgical tool by pulling on the surgical tool and pushing down on the guide wire.*

*21. A method of conducting a medical procedure using a guide wire, the method including:*

*contacting a surgical tool with a surgical site;*

*placing a guide wire having at least two deformable legs through the surgical tool, the deformable legs being in a first position in the surgical tool, the guide wire being monolithic and bifurcating into the two deformable legs at a distal end of the guide wire; and*

*inserting the deformable legs into the surgical site, the deformable legs moving to a second position when inserted in the surgical site,*

*wherein the deformable legs are separated a greater distance from each other in the second position than in the first position.*

*22. The method of claim 21, wherein the surgical site is a vertebral body.*

*23. The method of claim 21, wherein the two deformable legs are substantially linear, the deformable legs being substantially parallel to each other in the first position and diverging from a longitudinal axis of the guide wire in the second position.*

*24. The method of claim 21 wherein the surgical tool is a jamshidi needle.*

*25. The method of claim 21, further including the step of using the deformable legs as a marker or a stop for placing a second surgical tool.*

*26. A method of securing a guide wire in a surgical site, the method comprising:*

*placing a distal end of a surgical tool on a predetermined location on a surgical site, the surgical tool including a through bore having an bore diameter;*

*guiding a guide wire through the through bore; and*

*securing the guide wire to the surgical site by extending the guide wire beyond the distal end of the surgical tool;*

*wherein the guide wire is monolithic and bifurcates at a distal end of the guide wire into first and second substantially linear legs each having a free end, such that the distance between the free ends measured perpendicular to a longitudinal axis of the guide wire is less than or equal to the bore diameter when in the through bore and greater than the bore diameter when extended past the distal end of the surgical tool.*

*27. The method of claim 26, wherein the surgical site is a vertebral body.*

* * * * *